(12) United States Patent
Myougan et al.

(10) Patent No.: US 9,234,507 B2
(45) Date of Patent: Jan. 12, 2016

(54) STEAM CHARACTERISTICS AUTOMATIC MEASURING DEVICE AND GEOTHERMAL POWER-GENERATING DEVICE

(75) Inventors: Ichiro Myougan, Tokyo (JP); Yasuyuki Hishi, Takizawa-mura (JP); Toshiaki Aoki, Higashimurayama (JP)

(73) Assignees: Fuji Electric Co., Ltd., Kawasaki-shi (JP); Geothermal Engineering Co., Ltd., Tokyo (JP); Nikkiso Co., Ltd., Tokyo (JP)

( * ) Notice: Subject to any disclaimer, the term of this patent is extended or adjusted under 35 U.S.C. 154(b) by 775 days.

(21) Appl. No.: 13/120,532

(22) PCT Filed: Oct. 2, 2009

(86) PCT No.: PCT/JP2009/005112
§ 371 (c)(1),
(2), (4) Date: Jun. 13, 2011

(87) PCT Pub. No.: WO2010/038479
PCT Pub. Date: Apr. 8, 2010

(65) Prior Publication Data
US 2011/0239649 A1 Oct. 6, 2011

(30) Foreign Application Priority Data
Oct. 3, 2008 (JP) .................................. 2008-258362

(51) Int. Cl.
*F03G 7/04* (2006.01)
*G01N 27/08* (2006.01)

(52) U.S. Cl.
CPC ........ *F03G 7/04* (2013.01); *G01N 27/08* (2013.01); *Y02E 10/10* (2013.01)

(58) Field of Classification Search
CPC .................. G01N 27/08; G01N 25/60; G01N 2291/02836; Y02E 10/10; F03G 7/04
See application file for complete search history.

(56) References Cited

U.S. PATENT DOCUMENTS 3,420,775 A * 1/1969 Cadwallader ................. 210/718
3,422,674 A * 1/1969 Schroeter ................... 73/152.04
(Continued)

FOREIGN PATENT DOCUMENTS

JP 62222140 A 9/1987
JP 9206733 A 8/1997
(Continued)

OTHER PUBLICATIONS

Stapleton, M., "Scaling and Corrosion in Geothermal Operation," PowerChem Technology, (2002) Accessed online at <www.powerchemtech.com>.*
(Continued)

*Primary Examiner* — Lisa Caputo
*Assistant Examiner* — Punam Roy
(74) *Attorney, Agent, or Firm* — The Webb Law Firm

(57) ABSTRACT

Provided is a steam characteristics automatic measuring device capable of automatically, ideally also continuously measuring the characteristics of steam taken from a production well, without being affected by interfering components, such as hydrogen sulfide gas and carbon dioxide gas contained in large quantities in steam taken from under the ground, which enables the operator to continuously understand the characteristics of steam and support a smooth operation of a geothermal power plant. The device has a silica monitor for measuring a concentration of silica included in a condensate obtained by cooling steam taken from under the ground; an electrical conductivity meter for automatically measuring the electrical conductivity thereof; a pH meter for automatically measuring the pH value thereof; and a data processing transmitter for automatically transmitting data measured by each of the monitor and meters. A geothermal power-generating device equipped with the steam characteristics automatic measuring device is also provided.

15 Claims, 1 Drawing Sheet

(56) References Cited

U.S. PATENT DOCUMENTS

| | | | | |
|---|---|---|---|---|
| 3,757,516 | A * | 9/1973 | McCabe | 60/641.2 |
| 4,043,129 | A * | 8/1977 | McCabe et al. | 60/641.2 |
| 4,319,895 | A * | 3/1982 | Kemmer | 95/235 |
| 4,339,719 | A * | 7/1982 | Rhines et al. | 324/446 |
| 4,355,997 | A * | 10/1982 | Smith et al. | 436/25 |
| 4,402,910 | A * | 9/1983 | Smith et al. | 422/83 |
| 4,472,354 | A * | 9/1984 | Passell et al. | 422/62 |
| 4,661,459 | A * | 4/1987 | Hirtz | 436/25 |
| 4,739,647 | A * | 4/1988 | Monticelli, Jr. | 73/23.2 |
| 4,833,622 | A * | 5/1989 | Barto et al. | 700/271 |
| 4,844,162 | A * | 7/1989 | Maassen et al. | 166/267 |
| 4,930,316 | A * | 6/1990 | Bonham, Jr. | 60/641.5 |
| 5,038,567 | A * | 8/1991 | Mortiz | 60/641.5 |
| 5,085,782 | A * | 2/1992 | Gallup et al. | 210/696 |
| 5,413,718 | A * | 5/1995 | Gallup et al. | 210/696 |
| 5,595,717 | A * | 1/1997 | Harper et al. | 423/339 |
| 5,660,042 | A * | 8/1997 | Bronicki et al. | 60/641.5 |
| 5,665,242 | A | 9/1997 | Gallup | |
| 6,375,907 | B1 * | 4/2002 | Gallup | 423/571 |
| 6,416,672 | B1 * | 7/2002 | Midkiff | 210/714 |
| 6,666,971 | B2 * | 12/2003 | Chen | 210/687 |
| 6,976,397 | B2 * | 12/2005 | Widmer | 73/863.03 |
| 2006/0157420 | A1 * | 7/2006 | Hays et al. | 210/696 |
| 2008/0236616 | A1 * | 10/2008 | Bloch | 134/2 |
| 2009/0030553 | A1 * | 1/2009 | Hicks et al. | 700/266 |
| 2011/0144947 | A1 * | 6/2011 | Myougan et al. | 702/183 |
| 2012/0079880 | A1 * | 4/2012 | Freitag | 73/198 |
| 2012/0128469 | A1 * | 5/2012 | Kato et al. | 415/118 |

FOREIGN PATENT DOCUMENTS

| | | |
|---|---|---|
| JP | 11326310 A | 11/1999 |
| JP | 2002131261 A | 5/2002 |
| JP | 2011058981 A * | 3/2011 |

OTHER PUBLICATIONS

Meza, A., "Accurate online silica analyzers ensure boiler performance, add boiler life," Sep. 1, 2009. Accessed online at <http://www.powermag.com/catergory/gas/>.*

"Development of an Online Monitor for Geothermal Steam," Nikkiso Co., LTD. Available online 2000. Accessed online on Sep. 10, 2013 at <http://nikkiso.com/rd/main/015.html>.*

M. Hayakawa, "Outline of a Geothermal Power Generation", Oct. 2004, vol. 55, No. 10, p. 1027-1042.

New Zealand Office Action re Patent Application No. 519875.

* cited by examiner

STEAM CHARACTERISTICS AUTOMATIC MEASURING DEVICE AND GEOTHERMAL POWER-GENERATING DEVICE

TECHNICAL FIELD

The present invention relates to a steam characteristics automatic measuring device and a geothermal power-generating device. More particularly, the present invention relates to a steam characteristics automatic measuring device capable of automatically measuring the characteristics of steam taken out from a production well, without being affected by interfering components, such as hydrogen sulfide gas and carbon dioxide gas that are contained in large quantities in a steam taken from under the ground; and supporting the operation of a geothermal power plant based on measured values of the steam characteristics that have been automatically measured. The present invention also relates to a geothermal power-generating device capable of smooth geothermal power generation.

BACKGROUND ART

Power generating devices include geothermal power-generating devices other than thermal power-generating devices, hydroelectric power-generating devices and nuclear power-generating devices.

Geothermal power generation is carried out in the following way, as explained in non-patent document 1: Magma chambers with temperatures of around 1000° C. are located at a relatively shallow depth, several kilometers from the surface of the earth. Heat from the chambers heats rainwater that has permeated into the ground, which results in natural formation of a geothermal reservoir stratum in the earth. Into such a geothermal reservoir stratum is driven one or more pipes for production wells, the number of which is decided at need. A gas-liquid two-phase fluid-transferring tube is connected with the pipe, and gas-liquid two-phase fluid is transferred through the gas-liquid two-phase fluid-transferring tube to a steam separator. The fluid is divided into steam and hot water in the steam separator. The separated steam is sent through a steam pipe to a power-generating turbine. The steam introduced into the turbine rotates blades of the turbine, and the rotating power thus obtained rotates, in turn, the rotor of a generator. Electric power is thus obtained from the generator. On the other hand, hot water separated in the steam separator is sent through a hot water-returning tube to a reinjection well and returned deep in the ground.

Geothermal power plants are normally constructed in areas where geothermal reservoir strata are formed. Such areas are places often designated as national parks or called hot-spring resorts. Therefore it is difficult to employ staff members sufficient to operate a power plant and to construct installations and facilities necessary to operate a power plant.

A geothermal plant generates several tens kilowatts of electric power, which is small compared with several hundreds to a million kilowatts of electric power generated by a thermal power-generating plant. As a result, a geothermal power plant constructed at a remote and secluded place among the mountains is normally operated by a limited number of staff members for economic reasons.

It is difficult to control the characteristics of steam from one minute to the next in a geothermal power plant operated by a small number of staff members. Currently, control of the steam characteristics depends on, for example, a manual analysis that is carried out approximately once a month. More specifically, steam taken from a production well is cooled to condensate, and a water sample is taken out of the condensate. The water sample is sent to an analysis center, remote from the geothermal power plant, and the sample is manually analyzed at the center. It takes time for the staff members in the plant to have results of the manual analysis. Therefore when they find deterioration in the steam characteristics, the power-generating facilities may have already had trouble and operation of the geothermal power plant may have been fatally affected.

Problems with a power-generating turbine may include solid matter adhering to the blades of the turbine, or corrosion crack occurring in the surface of a blade caused by chloride ions, which may result in malrotation of the turbine blades. Another problem associated with operation of a geothermal power plant may be changes in the degree of vacuum in the condenser into which steam having worked in the turbine is sent, caused by unexpected changes in the amount of non-condensable gas in the steam. Generally, steam sent into a condenser is rapidly cooled to condensate, which creates a high degree of reduced pressure in the condenser. This high degree of reduced pressure increases revolutions of the turbine blades. In the field of geothermal power-generating devices, to bring the inside of the condenser into a high degree of reduced pressure is expressed as "to bring it into high vacuum". When steam introduced into the condenser contains non-condensable gas, the condenser is not brought into a high vacuum state, which leads to a decrease in revolutions of the power-generating turbine. Therefore the inclusion of non-condensable gas in steam that will be sent to the condenser decreases the efficiency of power generation by the power-generating turbine.

The inventors of the present invention observed the surface of the blades when the power-generating turbine had problems such as irregularity in or incapability of revolution. As a result, they found that solid matter adhered to the surface. They also observed the surface of the blades to find whether there were cracks in the surface, and the observation revealed that it had stress corrosion cracking caused by chloride ions.

The steam separated from vapor-liquid two-phase fluid drawn from a production well for geothermal power generation contains various minerals. It is considered that when such a steam is sprayed onto the blades of the turbine, solid matter adheres to the surface of the blades, and that an increase in the amount of the solid matter causes the malfunctions mentioned hereinbefore. Also, a decrease in the degree of vacuum in the condenser due to changes in the amount of non-condensable gas in the steam that has worked in the turbine invites deterioration in the power generation performance of the power-generating turbine, which seriously affects the efficiency of power generation.

Therefore has been desired a steam characteristics automatic measuring device for geothermal power generation, capable of continuously and automatically carrying out analysis of the characteristics of steam which is introduced into a power-generating turbine and a condenser in a geothermal power-generating device which is operated and controlled by a few staff members; and informing engineers of the characteristics of steam at a location remote from the geothermal power-generating device, as well as a geothermal power-generating device equipped with the measuring device.

Non-patent document 1: "Thermal and Nuclear Power Generation", by Thermal and Nuclear Power Engineering Society, the October, 2004 issue, page 7 and pages 10-14

DISCLOSURE OF THE INVENTION

Problems to be Solved by the Invention

As a result of the inventors' research, they found that solid matter adhering to the blades of a power-generating turbine when the turbine was rotated by steam for geothermal power generation taken out from a production well, which is also called scale, was made mainly from silica. The present invention was made based on this finding by the inventors.

So far, silica monitors are known as an analyzer for monitoring silica, a cause for scale, and ion chromatographs as a device for measuring the concentration of chloride ions that erode the surface of the blades of a turbine. However, steam taken from under the ground for geothermal power generation includes hydrogen sulfide. When a conventional ordinary silica monitor is used for the purpose of measuring the silica content included in steam taken out from under the ground, the measured value also includes the amount of hydrogen sulfide, which means that the silica content itself is not measured.

When a solution to be measured is a simple one that contains only chloride ions and counter cations, the electrical conductivity of a solution after removal of the counter cations from the initial solution provides the concentration of the chloride ions included in the initial solution. In this case, a standard curve showing the relationship between the electrical conductivity and the concentration of chloride ions is prepared in advance.

However, steam taken out from under the ground also includes a large amount of carbon dioxide gas. Therefore when steam taken out from under the ground is condensed to a condensate and the electrical conductivity of the condensate is measured, measurement of the electrical conductivity is carried out with carbonate ions originating from the dissolved carbon dioxide gas, chloride ions and other anions. Thus, the relationship between the electrical conductivity and the concentration of chloride ions is no longer pertinent to this measurement, and it cannot be said that the concentration of chloride ions is obtained from the electrical conductivity.

An objective of the present invention is to provide a steam characteristics automatic measuring device that supports operation of a geothermal power plant by automatically and continuously measuring the characteristics of steam for geothermal power generation taken out from under the ground in order to continuously grasp the conditions of the power-generating turbine and/or those of the condenser and to operate the geothermal power generation smoothly. A further objective is also to provide a geothermal power-generating device capable of operating geothermal power generation properly and smoothly.

Means to Solve the Problems

As means to achieve the aforementioned objectives, the present invention provides:
(1) A steam characteristics automatic measuring device comprising: a silica monitor for measuring a concentration of silica included in a condensate obtained by cooling steam taken out from under the ground; an electrical conductivity meter for automatically measuring an electrical conductivity of the condensate; a pH meter for automatically measuring a pH value of the condensate; and a data processing transmitter for automatically transmitting data measured by each of the silica monitor, the electrical conductivity meter and the pH meter;
(2) The steam characteristics automatic measuring device as described under item (1), wherein the device comprises an automatic non-condensable gas flowmeter for automatically and continuously measuring a total of a first flow rate of non-condensable gas separated from the steam by the cooling and a second flow rate of non-condensable gas separated from the condensate;
(3) The steam characteristics automatic measuring device as described under item (2), wherein the automatic non-condensable gas flowmeter is designed so as to automatically measure a volume of non-condensable gas included in the steam to be sent to the power-generating turbine from a flow rate of the condensate condensed by cooling the steam, and the total of the first flow rate and the second flow rate;
(4) The steam characteristics automatic measuring device as described under item (2) or (3), wherein the data processing transmitter has a functionality for automatically transmitting data measured by the automatic non-condensable gas flowmeter;
(5) The steam characteristics automatic measuring device as described under any one of items (1)-(4), wherein the device comprises an interfering component-removing device for removing interfering components in the condensate to be sent to the electrical conductivity meter;
(6) A steam characteristics automatic measuring device comprising an automatic non-condensable gas flowmeter for automatically and continuously measuring a total of a first flow rate of non-condensable gas separated from steam taken out from under the ground by cooling the steam and a second flow rate of a non-condensable gas separated from condensate obtained by cooling the steam;
(7) The steam characteristics automatic measuring device as described under item (6), wherein the automatic non-condensable gas flowmeter is designed so as to automatically measure a volume of non-condensable gas included in the steam to be sent to the power-generating turbine from a flow rate of the condensate condensed by cooling the steam, and the total of the first flow rate and the second flow rate;
(8) The steam characteristics automatic measuring device as described under item (6) or (7), wherein the data processing transmitter has a functionality for automatically transmitting data measured by the automatic non-condensable gas flowmeter; and
(9) A geothermal power-generating device comprises the steam characteristics automatic measuring device as described under any one of items (1)-(8).

Advantages of the Invention

Causes of hindrance to smooth rotation of a power-generating turbine may include adherence of silica to the blades of a turbine, which makes greater the difference between the pressure of the inside of a steam injection aperture for spraying steam onto the turbine and that of the outside of the aperture; corrosion of the blades of a power-generating turbine; a change in rotation of a power-generating turbine caused by cracking in the turbine; and a decrease in the degree of vacuum in a condenser caused by the existence of non-condensable gas.

Scale adhering to the blades of a power-generating turbine is mainly made from amorphous silica and minerals such as rock salt. When these causative substances are included in steam, they are in an ionic state and therefore they cannot be separated or removed by a steam separator. Also, when a steam separator does not function normally or even when a steam separator functions normally, part of drops included in steam may sometimes pass through a steam separator in the state of drops, which means that steam including the substances causative of scale is introduced into a power-generating turbine. Trouble such as corrosion and cracking in the surface of the blades of a power-generating turbine may be caused by chemical corrosion by strong acid components in an ionic state existing in the steam and stress corrosion. Monitoring the amount of strong acid components in steam may prevent or protect the blades of a power-generating turbine from chemical corrosion. Also, it is known that stress corrosion in the blades of a power-generating turbine is related to the concentration of anions, especially that of chloride ions, in steam, and the pH value. Monitoring the concentration of chloride ions and the pH value may prevent or protect the blades of a power-generating turbine from stress corrosion.

Therefore the measurement of the silica content and the concentration of anions included in a condensate obtained by cooling steam, and that of the pH value of the condensate provide the characteristics of steam sprayed onto a power-generating turbine. The conditions for operating a geothermal generation plant may be adjusted based on the measured values.

In more detail, the amount of scale adhering to the blades of a power-generating turbine may be estimated based on the measured concentration of silica in the condensate. Also, the amount of anions in steam may be estimated from the measured electrical conductivity of the condensate whose cations and carbonates have been removed with a device such as an ion-exchange resin. Furthermore, since inorganic salts such as sodium chloride are included in steam, the amount of anions provides the amount of inorganic salts including sodium chloride. Monitoring changes in the amount of strong acid components in steam may be carried out by continuous measurement of the pH value in the condensate.

The rotating performance of a power-generating turbine is affected by the amount of non-condensable gas included in steam that is sprayed onto the blades thereof.

Steam that has been sprayed onto a power-generating turbine to rotate the turbine is sent to a condenser where the steam is condensed to condensate. Non-condensable gas that is included in the steam remains in the condenser in the form of gas as it is. A decrease in the degree of vacuum in the condenser depending on the amount of the remaining non-condensable gas affects the difference between the pressure inside the spraying nozzle and that outside it, which results in a change in the rotating power of the turbine, which further exerts an influence on the efficiency of power generation.

Therefore measurement of the amount of non-condensable gas included in steam contributes to improvement in the efficiency of power generation.

The present invention includes an automatic measurement of the concentration of silica included in a condensate, which cooling of the steam supplied to the power-generating turbine has provided, with a silica monitor; an automatic measurement of the electrical conductivity of the condensate with an electrical conductivity meter; and an automatic measurement of the pH value of the condensate with a pH meter, which enables the operator to understand the characteristics of steam continuously and to estimate influence on the power-generating turbine by the steam based on the measured concentration of silica, the measured electrical conductivity and the measured pH value. Thus, the present invention provides a steam characteristics automatic measuring device capable of supporting the operation of geothermal power generation based the estimation.

The present invention also provides a steam characteristics automatic measuring device capable of automatically and continuously measuring the amount of non-condensable gas in steam and adjusting the conditions in the condenser to improve the efficiency of power generation.

A steam characteristics automatic measuring device according to the present invention is placed in a geothermal power plant, while a data receiving-processing facility named, for example, Electric Power Plant Control Center, Electric Power Plant Control Room or the Headquarters of the Electric Power Plant, to receive data from the steam characteristics automatic measuring device, analyze the data and output commands for controlling the power plant, may be located in an area where it is easy to employ staff members and construct the facility, such as an urban area or an industrial area. Then, it is possible to automatically receive the silica content, the electrical conductivity and the pH value, as well as the amount of non-condensable gas at the facility. This data receiving-processing facility removes the necessity of manually collecting the data at the geothermal power plant. The facility also relieves the staff members from going all the way to the geothermal power plant and enables them to know the characteristics of steam just by analyzing the continuously collected data.

A computing unit for calculating the concentration of anions from data outputted by the electrical conductivity meter may be placed either in the geothermal power plant or the data receiving-processing facility.

Support for the operation of geothermal power generation realized by automatic and continuous measurement of the silica content, the electrical conductivity and the pH value as well as the amount of non-condensable gas may include:
(1) Control of the amount of steam sent to the steam separator, or hot water separator,
(2) Control of the efficiency of steam separation by changing the amount of water supplied to the steam separator,
(3) Control of the amount of an acid to be added to hot water separated from the steam in order to prevent silica from adhering to the inner walls of the devices and pipes,
(4) Control of the operation of a device for producing a vacuum in the condenser that evacuates the condenser,
(5) Bypass operation of the power-generating turbine,
(6) Changing the number of production wells from which gas-liquid two-phase fluid is taken out, and
(7) Control the amount of gas-liquid two-phase fluid taken out from the production wells.

Changes in the operating conditions of a geothermal power plant are capable of preventing scale from accumulating on the blades of a power-generating turbine, keeping the blades of a power-generating turbine from corrosion and cracks therein, and enhancing the degree of vacuum in the condenser, thereby improving the efficiency of rotation of the power-generating turbine.

BEST MODE TO CARRY OUT THE INVENTION

Figure 1:
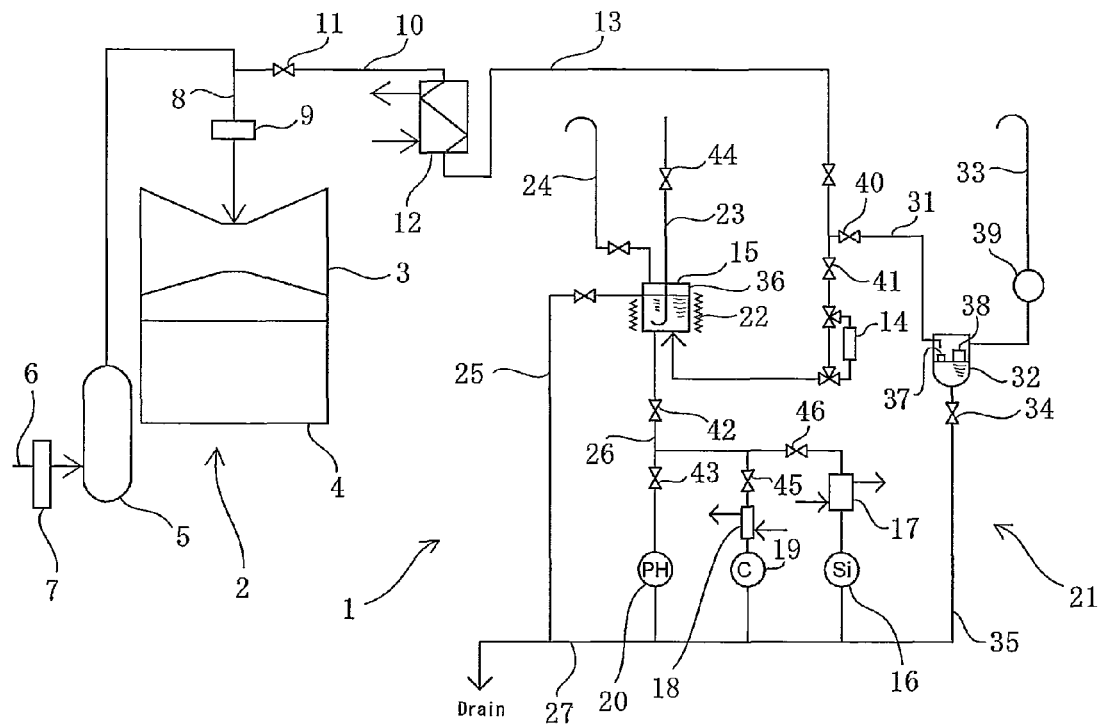
FIG. 1 is an illustration showing a first example of the present invention.

Firstly, we will provide a general explanation of a geothermal power generation system.

A geothermal power plant has a production well, a steam separator for dividing gas-liquid two-phase fluid taken out from the production well into hot water and steam, a power-generating turbine that is rotated by a jet of the steam separated by the steam separator, a generator for generating electricity by rotation of the rotors that are turned by the rotation of the shaft of the power-generating turbine, and a condenser for producing reduced pressure as low as possible, especially essentially a vacuum, at around the turbine exit by condensing the steam to water in order to make maximum the work of rotation of the power-generating turbine.

A production well is normally a well from which high-temperature high-pressure hot water or steam is taken out, from a geothermal reservoir stratum at a depth from several hundred meters, for example 300 m, to several thousand meters, for example 3000 m, from the surface of the earth. Either of hot water or steam may sometimes be taken out from the geothermal reservoir stratum. On the other hand, gas-liquid two-phase fluid, which is a mixture of steam and hot water, may sometimes be taken out. A production well from which gas-liquid two-phase fluid is taken out is sometimes called a steam well.

Gas-liquid two-phase fluid is divided into steam and hot water in the steam separator. In another method of geothermal power generation, when hot water is taken from a production well, the hot water is divided into steam and hot water by, for example, reducing the pressure of the taken hot water. Steam is used to rotate the power-generating turbine, while the hot water is returned to the earth through a reinjection well.

The geothermal power-generating system in a geothermal power plant has a water-dominated flash cycle including a single flash cycle and a double flash cycle, and a superheated steam flash cycle.

In a geothermal power-generating system operating on a single flash cycle, steam separated in the steam separator is sprayed onto the blades of the power-generating turbine.

A geothermal power-generating system operating on a double flash cycle, the steam separator has a first steam separator and a second steam separator. The first steam separator is sometimes called a high-pressure separator, while the second one a low-pressure separator.

High-temperature high-pressure hot water and steam, or liquid-gas two-phase fluid, supplied from the production well is sent to the first steam separator. High-temperature high-pressure steam (primary steam) separated in the first steam separator is sent toward the blades of the power-generating device through a scrubber or not through a scrubber, and is sprayed onto them. Hot water separated in the first steam separator is sent to the second steam separator.

To hot water sent from the first steam separator to the second steam separator is added an acid, for example, sulfuric acid, if necessary. The addition of an acid to hot water being transferred to the second steam separator is made in order to make slow the polymerization velocity of silica and prevent silica from adhering the inner walls of devices and pipes before the water is returned to a reinjection well. In the second steam separator, the hot water is further divided into water and high-temperature steam (or secondary steam) at a lower pressure. Separated water is sent and returned to a reinjection well. The separated secondary steam is sent to the blades of the power-generating turbine, if necessary through a demister, and sprayed onto them.

The portion placed at the position at which the primary steam, which is separated in the first steam separator, is sprayed onto the blades of the power-generating turbine is called a high-pressure turbine. This portion is different from the second portion at which the secondary steam, which is separated in the second steam separator, is sprayed onto the blades thereof and is called a low-pressure turbine.

The first steam jet and the second steam jet turn the power-generating turbine, which rotates the rotor of the generator. The rotation of the rotor surrounded by the stator causes electromagnetic induction, and thus power generation is carried out.

On the other hand, steam which has been supplied to the power-generating turbine and has done the work of rotating it is sent to the condenser. High-temperature steam is cooled and condensed to water in the condenser. When higher-temperature steam is condensed to water, the pressure in the condenser is highly reduced and the pressure at the turbine exit becomes smaller than the pressure at the turbine entrance. Water produced in the condenser is, for example, sent to a cooling tower and is reused to cool steam. When high-temperature steam is returned to water, non-condensable gas that has been included in the steam remains gaseous. The remaining non-condensable gas is discharged from the condenser through an ejector.

The ejector introduces part of the high-temperature steam that has been separated in the first separator into a narrow pipe in the ejector. The steam, jetting out of the narrow pipe at a high velocity, draws the gas in the condenser out of it.

The high-temperature steam and the gas having been in the condenser, both discharged through the ejector, are separated in a gas-liquid separator. The separated water is returned to the condenser or sent to the cooling tower. The separated gas is discharged, for example, to the atmosphere.

The steam characteristics automatic measuring device according to the present invention is incorporated into a geothermal power-generating system with such a structure as that explained hereinbefore.

We will explain the present invention, referring to a steam characteristics automatic measuring device shown in FIG. 1, an example of the present invention.

As shown in FIG. 1, a geothermal power-generating device 2, into which the steam characteristics automatic measuring device 1 is incorporated, has a generator (not shown in the figures); a power-generating turbine 3 equipped with a shaft (not shown in the figures) connected with the axle of a rotor that the generator has, and several rotating blades and a fixed nozzle (not shown in the figures) attached to the shaft; a gas-liquid separator 5 for receiving gas-liquid two-phase fluid drawn from a production well and dividing the fluid into hot water and high-temperature steam; and a condenser 4 for transforming steam that has been sprayed onto the rotating blades to water.

The production well and the gas-liquid separator 5 are connected with first piping 6, through which high-temperature liquid-gas two-phase fluid is sent to the gas-liquid separator 5. A water spray 7 is inserted in the first piping 6 just before the gas-liquid separator 5 in the direction of fluid flow. Water supplied to the first piping 6 with the water spray 7 changes the efficiency of division between hot water and high-temperature steam in the gas-liquid separator 5.

The gas-liquid separator 5 and a steam-supplying nozzle (not shown in the figures) are connected with second piping 8. The high-temperature steam, which has been separated in the gas-liquid separator 5, is sent through the second piping 8 to the steam-supplying nozzle, and is sprayed from the steam-supplying nozzle onto the blades of the power-generating turbine. A second spray 9 is inserted in the second piping 8 just before the steam-supplying nozzle in the direction of fluid flow. Supply of water sent through the second spray 9 to the power-generating turbine 3 by the steam-supplying nozzle makes it possible to remove scale formed on the blades of the power-generating turbine. The water supply also serves to make drops included in the steam grow to let them adsorb silica, so that it is difficult for silica to adhere to the blades. However, because supplied water cools the steam, which lowers the efficiency of power generation, the water supply should preferably be restricted to the irreducible minimum of a demand.

The steam-supplying nozzle (not shown in the figures) is arranged in such a way in relation to the power-generating turbine 3 that steam is sprayed onto the blades of the turbine.

The shaft of the power-generating turbine 3 is coaxially coupled with the axle of the generator or coupled via a power transmitter with it. When the power-generating turbine 3 turns, the rotor of the generator also rotates, and the rotation of the rotor causes electric current in the coils on the stator.

The second piping 8 connecting the gas-liquid separator 5 with the steam-supplying nozzle has third piping 10 branched from the second piping 8 at a location upstream of the second spray 9. An on-off valve 11 is placed in the third piping 10. The piping 10 is connected with a cooler 12.

The cooler 12 is also called a sample cooler. The cooler 12 cools steam sampled through the third piping 10. The cooled steam turns to a mixture of condensate resulting from the condensation and non-condensable gas remaining gaseous because it is not condensed. Part of the non-condensable gas that has not been vaporized is dissolved in the condensate.

With the cooler 12 is coupled fourth piping 13. The mixture of the condensate obtained by the cooling in the cooler 12 and the non-condensable gas is transferred to the steam characteristics automatic measuring device 1 through the fourth piping 13.

The steam characteristics automatic measuring device 1 to be installed in the geothermal power-generating device 2 has a cation remover 14, a degasifying treatment unit 15, a silica monitor 16, a cooling unit 17, a degasifier 18, an electrical conductivity meter 19, a pH meter 20, and an automatic non-condensable gas flowmeter 21.

The system including the cation remover 14, the degasifying treatment unit 15, the silica monitor 16, the cooling unit 17, the degasifier 18, the electrical conductivity meter 19, and the pH meter 20 may be called a chemical composition-measuring system, while a series of devices including the automatic non-condensable gas flowmeter 21 may sometimes be called a non-condensable gas-measuring system.

In the steam characteristics automatic measuring device 1 shown in FIG. 1, the cation remover 14 is placed in a bypass of the fourth piping 13, through which the mixture produced by the cooling in the cooler 12 is transferred. This cation remover 14 is normally a packed tower or packed column filled with anion-exchange resin. When the mixture is allowed to pass through the cation remover 14, cations dissolved in the condensate of the mixture are removed, which leads to a change of a carbonate, having existed in the form of a bicarbonate compound in the condensate before treated with the cation remover 14, to bicarbonate ions, which are further changed to dissolved carbon dioxide gas. Furthermore, the cation-removed mixture with dissolved carbon dioxide gas is degasified in the degasifying treatment unit 15, and the dissolved carbon dioxide gas is removed in the degasifier 18. As a result, carbonate components that interfere the measurement of the electrical conductivity of the condensate are removed from the condensate. Therefore the combination of the cation remover 14 and the degasifying treatment unit 15 is an example of the interfering component-removing device of the present invention.

The degasifying treatment unit 15 receives the mixture which has been transferred through the fourth piping 13, and has passed through the cation remover 14, or has not passed through the cation remover 14 according to circumstances. Subsequently, the degasifying treatment unit heats the condensate of the mixture to a predetermined temperature, while the unit blows nitrogen gas into the heated condensate and allows the gas to bubble up. The carbon dioxide gas and hydrogen sulfide gas are removed through the bubbling.

As understood, the degasifying treatment unit 15 is equipped with a sample tank 36, a heater 22 for heating the condensate stored in the sample tank 36, and a nitrogen gas-introducing pipe 23 through which nitrogen gas is blown into the condensate stored in the sample tank 36. The degasifying treatment unit 15 is further provided with a vent 24 for discharging the removed gas, a first discharging pipe 25 for discharging an excessive portion of the condensate by letting it flow into the pipe when the amount of the condensate in the sample tank 36 exceeds a predetermined amount, and fifth piping 26 for transferring the condensate after it is degasified.

The fifth piping 26 is branched into three subsidiary pipings: The first subsidiary piping is connected to the cooling unit 17, which is subsequently connected to the silica monitor 16.

There is no special limitation on the silica monitor 16, as long as it is capable of measuring the concentration of silica dissolved in the condensate. An example may be a silica monitor according to molybdenum-blue spectrophotometry. A specific example of the silica monitor may be a model 7180 silica monitor marketed by Nikkiso Co., Ltd. This silica monitor is a measuring device employing molybdenum-blue spectrophotometry according to JIS K0101, and the shortest time necessary for the device to measure a concentration of silica is five minutes.

Figure 2:
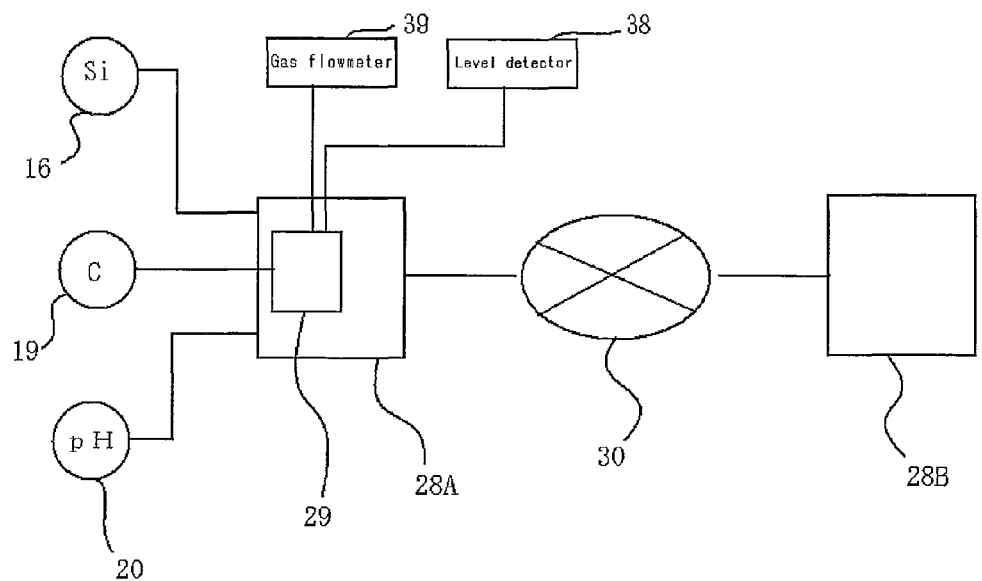
FIG. 2 is an illustration showing a second example of the present invention.

As shown in FIG. 2, the silica monitor 16 outputs the measured silica content in the form of an electric signal and sends the signal to a data processing transmitter 28A.

The condensate that has passed through the silica monitor 16 is discharged to a drain through sixth piping 27.

The second subsidiary piping, one of the three subsidiary pipings branched from the fifth piping 26, is connected with the degasifier 18. The condensate after degasification in the degasifier 18 is introduced into an electrical conductivity meter 19.

The degasifier 18 is a device which allows the condensate to contact a gas that does not contain carbon dioxide gas with a hollow fiber membrane in between and removes dissolved carbon dioxide gas from the condensate by means of a difference in the concentration of carbon dioxide gas between the condensate and the gas.

There is no special limitation on the electrical conductivity meter 19 especially concerning the method of the measurement and the kind of the device, as long as it is capable of measuring the electrical conductivity of the condensate.

A suitable one may be selected from commercial electrical conductivity meters.

As shown in FIG. 2, the electrical conductivity meter 19 outputs the measured electrical conductivity in the form of an electric signal and sends the signal to a data processing transmitter 28A.

The condensate that has passed through the electrical conductivity meter 19 is discharged to the drain through the sixth piping 27.

The third subsidiary piping, one of the three subsidiary pipings branched from the fifth piping 26, is connected with the pH meter 20. There is no special limitation on the pH meter 20 especially concerning the method of the measurement and the kind of the device, as long as it is capable of measuring the pH value of the condensate. A suitable one may be selected from commercial pH meters.

As shown in FIG. 2, data outputted by the electrical conductivity meter 19 are inputted into the data processing transmitter 28A. The condensate whose electrical conductivity is measured by the electrical conductivity meter 19 has been treated with the degasifying treatment unit 15 and the degasifier 18, and carbon dioxide gas and hydrogen sulfide gas have been removed from it. Also, cations having been included in the condensate have been removed with the cation remover 14. As a result, when the electrical conductivity of the condensate, from which the carbon dioxide gas, hydrogen sulfide gas and cations have been removed, is measured with the electrical conductivity meter 19, the electrical conductivity in proportion to the concentration of chloride ions that have not been removed but remain in the concentrate is measured. What should be mentioned here is that the steam taken from the production well includes sulfuric acid. However, because sulfuric acid is a non-volatile substance, the condensate, which is obtained by the cooling of the condensate separated in the gas-liquid separator 5, seldom includes sulfuric acid. Therefore it can be supposed that the condensate to be measured includes such a trivial amount of sulfuric acid that it can be ignored. Thus, it can be inferred that the measured electrical conductivity represents the amount of chloride ions as anions included in the high-temperature steam.

The data processing transmitter 28A is provided with a processor 29. The processor 29 is a calculating unit in the present invention. The processor 29 calculates the concentration of chloride ions from the electrical conductivity measured by the electrical conductivity meter 19 according to, for example, the following conversion equation:

Equation (1):

$$\text{Concentration of anions (or concentration of chloride ions) (ppb)} = \text{Electrical conductivity } (\mu S/cm)/12.071 \times 100 \quad (1)$$

In the equation, "12.071" is an example of the constant. The constant is suitably decided based on analysis of the characteristics of the steam produced at the place where a geothermal power plant is located.

The data processing transmitter 28A transmits data of the silica content, data of the amount of anions, which obtained from the electrical conductivity, and data of the pH value to a receiver 28B placed in the operation supporting facility, or the receiving-processing facility, through a telecommunications system 30 such as the Internet or a telephone leased line. This operation supporting facility may be located in an area where it is easy to employ staff members who are able to support the operation, such as workers and operators, and it is easy for them to lead a normal daily life, unlike the area where a geothermal power plant is located. The data processing transmitter 28A corresponds to the data processing transmitter according to the present invention.

On the other hand, the non-condensable gas measuring system has an automatic non-condensable gas flowmeter 21 to which the mixture is transferred through seventh piping 31 branched from the fourth piping 13, as shown in FIG. 1.

Various arrangements may be employed for the automatic non-condensable gas flowmeter 21, as long as they are capable of measuring the amount of non-condensable gas included in the steam. In the example shown in FIG. 1, the flowmeter is composed of a thermometer 37 for measuring the temperature of the condensate being introduced, a tank 32 in which the condensate introduced is stored, a level detector 38 with which the tank 32 is provided at the inside thereof, a gas-discharging pipe 33 for discharging the gas in the tank 32, a gas flowmeter 39 for measuring the flow rate of the discharged gas, and a second discharging pipe 35 with an automatic drain valve 34, for discharging the liquid in the tank 32.

Vessels capable of receiving a mixture produced by the cooling of steam and capable of separating non-condensable gas in the form of a gas, which has been included in the steam, will serve as the tank 32. For example may be employed a drain pot with a structure including an impact plate, which utilizes an inertial impaction technique in which a mixture of drops and gas are forced to impact an obstacle whereby the drops are separated from gas.

The automatic non-condensable gas flowmeter 21 measures the temperature of the condensate with the thermometer 37 first, and subsequently it separates non-condensable gas from the mixture in the tank 32. The separated non-condensable gas is discharged to the atmosphere through the gas-discharging pipe 33, and the amount of the discharged gas is measured with the gas flowmeter 39. As shown in FIG. 2, data corresponding to the flow rate of the discharged non-condensable gas measured with the flowmeter 39 are outputted and sent to the processor 29. When the level detector 38 judges that a predetermined amount of the condensate is stored in the tank 32, the automatic drain valve 34 opens automatically to let the condensate flow out of the tank into the second discharging pipe 35. When the level detector 38 detects that the liquid level falls to the lowest, it outputs a lowest level-detecting signal and sends it together with the time of the detection to the processor 29. On the other hand when the level detector 38 detects that the liquid level rises to the highest, it outputs a highest level-detecting signal and sends it together with the time of the detection to the processor 29.

The processor 29 calculates the amount of the non-condensable gas based on the data sent by the level detector 38 and the data sent by the gas flowmeter 39, for example, in the following way.

What we should mention here is that almost all of the non-condensable gas included in the steam is composed of carbon dioxide gas and hydrogen sulfide gas, and the presence of other gas components can be ignored because the amount of them is extremely small. When the composition of the non-condensable gas components included in the steam is analyzed in advance, the result of the analysis should be utilized as a condition for calculating the amount of the dissolved gas in order to improve the accuracy of the measurement.

Flow rate of water sample: A

Volume of the condensate when the surface thereof is at the highest level: B

Volume of the condensate when the surface thereof is at the lowest level: C

Time period necessary for the condensate level to rise from the lowest to the highest: D Equation for calculating the flow rate of the condensate:

$$A = (C-B)/D \quad (2)$$

Flow rate of the non-condensable gas: E

Flow rate value indicated by the gas flowmeter: F

Flow rate of saturated dissolved gas in the condensate: G (The value varies depending on the temperature under atmospheric pressure.)

Flow rate of the non-condensable gas:

$$E = F + G \quad (3)$$

Proportion H of the flow rate of the non-condensable gas to that of the condensate:

$$H = E/A \quad (4)$$

The data processing transmitter 28A transmits the amount of the non-condensable gas in the form of the proportion H of the flow rate of the non-condensable gas to that of the condensate, which the processor 29 calculates, to the receiver 28B.

The operation of the steam characteristics automatic measuring device with the structure described hereinbefore will be explained in the following.

The steam characteristics automatic measuring device shown in FIG. 1 is capable of measuring the pH value of a condensate, the silica content included in the condensate, and the electrical conductivity of the condensate at different times. Changes in the structure of the device enable the device to measure them simultaneously. The changes necessary for the simultaneous measurements will be mentioned hereinafter when occasions arise.

The device will be operated in the following way when the silica content is measured.

High-temperature steam transferred through the third piping 10 is cooled in the cooler 12, and is transformed into a mixture of liquefied condensate and non-condensable gas that is not liquefied. The mixture is introduced into the degasifying treatment unit 15 through the fourth piping 13, without having passed through the cation remover 14, or with having passed through the cation remover 14. A valve 40 is closed during this transference. The mixture is sent to the degasifying treatment unit 15 as it is for a predetermined time period. A portion of the condensate exceeding a predetermined level is discharged from the first discharging pipe 25. After the predetermined time period, a valve 41 is closed, which stops the sending of the mixture to the degasifying treatment unit 15. Subsequently, the valve 40 is opened, which results in transference of the mixture through the fourth piping 13 and the seventh piping 31 into the tank 32 of the automatic non-condensable gas flowmeter 21. As another result, the mixture in the degasifying treatment unit 15 is contained therein. Then, the condensate in the degasifying treatment unit 15 is heated with the heater 22 to a predetermined temperature, while nitrogen gas is blown into the condensate through the nitrogen gas-introducing pipe 23 and allowed to bubble up. The bubbling of the nitrogen gas separates hydrogen sulfide in the form of gas from the condensate in the degasifying treatment unit 15. The reason for the removal of hydrogen sulfide from the condensate is to prevent a reagent used in the silica monitor 16 from reacting with the hydrogen sulfide. After the completion of the degasification, valves 42 and 46 are open, and the degasified condensate in the degasifying treatment unit 15 is sent to the cooling unit 17 through the fifth piping 26. Valves 43 and 45 are closed at this stage. In the cooling unit the degasified condensate is cooled down to a predetermined temperature. The cooled is introduced into the silica monitor 16 where the silica content is measured and the measured value is sent to the data processing transmitter 28A.

The data representing the silica content that has been sent to the data processing transmitter 28A in the form of an electric signal is transferred to the receiver 28B through the telecommunications system 30, for example, the Internet or a telephone leased line.

When the pH value is measured, a mixture of the condensate and the non-condensable gas, obtained by liquefaction through the cooling in the cooler 12, is sent to the degasifying treatment unit 15 through the fourth piping 13, without having passed through the cation remover 14. When the pH value is measured, the degasifying treatment unit 15 does not carry out the same degasifying treatment with the condensate as with a condensate to be sent to the silica monitor 16, but carries out a foam separation treatment for dividing the mixture transferred through the fourth piping 13 into condensate and gas to remove non-condensable gas such as hydrogen sulfide gas. After the completion of the foam separation treatment in the degasifying treatment unit 15, the valves 42 and 43 are opened. The condensate that has undergone the foam separation treatment in the degasifying treatment unit 15 is sent to the pH meter 20 through the fifth piping 26.

The pH value of the condensate measured with the pH meter is sent to the data processing transmitter 28A.

The data corresponding to the pH value having been sent to the data processing transmitter 28A is transferred to the receiver 28B through the telecommunications system 30, for example, the Internet or a telephone leased line.

When the electrical conductivity of the condensate is measured, a mixture of a condensate and non-condensable gas is not directly sent to the degasifying treatment unit 15 but sent to the cation remover 14 in advance where cations in the condensate of the mixture are removed.

This cation remover is an example of the interfering component-removing device. The mixture of the condensate and the non-condensable gas after the removal of cations in the cation remover 14 is sent to the degasifying treatment unit 15. Carbon dioxide in the condensate from which cations have been removed changes to bicarbonate ions, which further change to dissolved carbon dioxide gas. A mixture of a condensate including the dissolved carbon dioxide gas and non-condensable gas is fed to the gasifying treatment device 15 for a predetermined time period. A portion of the condensate exceeding a predetermined level is discharged from the first discharging pipe 25.

After the predetermined time period, a valve 41 is closed, which stops the sending of the mixture to the cation remover 14 and the degasifying treatment unit 15. As a result, the mixture transferred through the fourth piping 13 is sent through the seventh piping 31 to the tank 32 of the automatic non-condensable gas flowmeter 21. As another result, the condensate in the degasifying treatment unit 15 is contained therein.

Then, the condensate in the degasifying treatment unit 15 is heated with the heater 22 to a predetermined temperature, while nitrogen gas is blown into the condensate through the nitrogen gas-introducing pipe 23 and allowed to bubble up. The bubbling of the nitrogen gas separates carbon dioxide gas and hydrogen sulfide gas from the condensate in the degasifying treatment unit 15. This degasifying treatment unit is also an example of the interfering component-removing device. The degasifying treatment unit 15 carries out degasification, utilizing the transference of carbon dioxide gas to the nitrogen gas due to the difference between the partial pressure of the nitrogen gas and that of the carbon dioxide gas included in the condensate caused by the bubbling of the nitrogen gas in the condensate. If the commencement and stoppage of the nitrogen gas supply is linked with the opening and closing of an automatic valve 44 placed in the inlet of a bubbling nozzle, it will reduce the consumption of nitrogen gas. After the completion of the degasification that has been carried out for the predetermined time period, the valves 42 and 45 are open, with the valves 43 and 46 closed. Then the degasified condensate in the degasifying treatment unit 15 is sent through the fifth piping 26 to the degasifier 18 where further degasification of carbon dioxide gas is carried out. The condensate from which carbon dioxide gas is further removed is introduced into the electrical conductivity meter 19 where the electrical conductivity of the condensate is measured and the measured value in the form of an electric signal is sent to the processor 29 of the data processing transmitter 28A.

The processor 29 calculates the concentration of chloride ions, for example, according to equation (1) explained hereinbefore. The data representing the calculated concentration of chloride ions in the form of an electric signal are transferred to the receiver 28B through the telecommunications system 30, for example, the Internet or a telephone leased line.

The silica content, the electrical conductivity and the pH value are measured one by one at different times in the method explained hereinbefore. This procedure results from the fact that the device has the only degasifying treatment unit 15. When the silica content, the electrical conductivity and the pH value are measured simultaneously, the silica monitor 16, the electrical conductivity meter 19 and the pH meter 20 should have an individual degasifying treatment unit.

On the other hand, the amount of the non-condensable gas is measured with the automatic non-condensable gas flowmeter 21 to which the mixture is sent through the fourth piping 13 and the seventh piping 31.

The automatic non-condensable gas flowmeter 21 measures the temperature of the mixture with the thermometer 37 first, and subsequently it separates non-condensable gas from the mixture in the tank 32. The non-condensable gas, originating from the one included in the mixture, is discharged to the atmosphere in the form of gas through the gas-discharging pipe 33, and the amount of the discharged gas is measured with the gas flowmeter 39. As shown in FIG. 2, data corresponding to the flow rate of the discharged non-condensable gas measured with the flowmeter are outputted and sent to the processor 29. When the level detector 38 judges that a predetermined amount of the condensate is stored in the tank 32, the automatic drain valve 34 opens automatically to let the condensate flow out of the tank into the second discharging pipe 35. When the level detector 38 detects that the liquid level falls to the lowest, it outputs a lowest level-detecting signal and sends it together with the time of the detection to the processor 29. On the other hand when the level detector 38 detects that the liquid level rises to the highest, it outputs a highest level-detecting signal and sends it together with the time of the detection to the processor 29.

The processor 29 calculates the amount of the non-condensable gas based on the data sent by the level detector 38, the data sent by the gas flowmeter 39, and the data outputted by the thermometer 37 according to, for examples equations (2)-(4).

The data processing transmitter 28A transmits the amount of the non-condensable gas in the form of the proportion H of the flow rate of the non-condensable gas to that of the water condensate, which the processor 29 calculates, to the receiver 28B.

In the facility where the receiver 28B is placed, the transmitted silica content, pH value, amount of anions based on the electrical conductivity such as the amount of chloride ions, and amount of the non-condensable gas are shown on a display or some other displaying units continuously or at regular intervals.

The conditions of the power-generating turbine in the geothermal power plant located far away are capable of being estimated. Knowing the amount of the non-condensable gas and other measured values, the staff members are able to estimate the degree of vacuum inside the condenser 4. The receiver 28 and the display are placed in a geothermal power generation-supporting facility, named, for example, Geothermal Power Generation Control Center, or Geothermal Power Generation Support Center, which is located in an area where it is easy for staff members, such as workers, operators, observers and controllers, to work and the traffic is convenient.

The operating conditions of the geothermal power plant may be changed based on the estimations through the selection of one or more of the following controls:
(1) Control of the amount of steam sent to the steam separator, or hot water separator,
(2) Control of the efficiency of steam separation by changing the amount of water supplied to the steam separator,
(3) Control of the amount of an acid to be added to hot water separated from the steam in order to prevent silica from adhering to the inner walls of the devices and pipes,
(4) Control of the operation of a device for producing a vacuum in the condenser that evacuates the condenser,
(5) Bypass operation of the power-generating turbine,
(6) Changing the number of production wells from which gas-liquid two-phase fluid is taken out, and
(7) Control the amount of gas-liquid two-phase fluid taken out from the production wells.
(8) Changing the number of production wells in operation.

Control through this selection is capable of preventing scale from adhering to the blades of the power-generating turbine and keeping the degree of vacuum high in the condenser, thereby improving the efficiency of power generation.

EXPLANATION OF REFERENCE NUMERALS

1: steam characteristics automatic measuring device
2: geothermal power-generating device
3: power-generating turbine
4: condenser
5: gas-liquid separator
6: first piping
7: water spray
8: second piping
9: second spray
10: third piping
11: on-off valve
12: cooler
13: fourth piping
14: cation remover
15: degasifying treating unit
16: silica monitor
17: cooling unit
18: degasifier
19: electrical conductivity meter
20: pH meter
21: automatic non-condensable gas flowmeter
22: heater
23: nitrogen gas-introducing pipe
24: vent
25: first discharging pipe
26: fifth piping
27: sixth piping
28A: data processing transmitter
28B: receiver
29: processor
30: telecommunications system
31: seventh piping
32: tank
33: gas-discharging pipe
34: automatic drain valve
35: second discharging pipe

We claim:
1. A steam characteristics automatic measuring device comprising:
a silica monitor for measuring a concentration of silica included in a condensate obtained by cooling steam taken out from under the ground, wherein the steam is divided into non-condensable gas and the condensate by the cooling;

an electrical conductivity meter for automatically measuring an electrical conductivity of the condensate;

an automatic non-condensable gas flowmeter for automatically and continuously measuring a flow rate of the non-condensable gas comprising a thermometer for measuring a temperature of the condensate;

a level detector for detecting a liquid level of the condensate and for outputting a lowest level-detecting signal when the liquid level falls to a lowest level and outputting a highest level-detecting signal when the liquid level rises to a highest level;

a processor for calculating a flow rate of saturated dissolved gas in the condensate based on the temperature, wherein the processor calculates a total flow rate of the non-condensable gas and the dissolved gas by adding the flow rate of non-condensable gas to the flow rate of saturated dissolved gas; and a data processing transmitter for automatically transmitting data measured by each of the silica monitor, the electrical conductivity meter and data corresponding to the total flow rate calculated by the processor.

2. The steam characteristics automatic measuring device according to claim 1, wherein the processor calculates the amount of the dissolved gas from a flow rate of the condensate, the temperature, and a saturation concentration of the dissolved gas at the temperature.

3. The steam characteristics automatic measuring device according to claim 2, wherein the device comprises an interfering component-removing device for removing interfering components in the condensate to be sent to the electrical conductivity meter.

4. The steam characteristics automatic measuring device according to claim 1, wherein the device comprises an interfering component-removing device for removing interfering components in the condensate to be sent to the electrical conductivity meter.

5. The steam characteristics automatic measuring device according to claim 4, wherein the interfering component-removing device includes a cation remover for removing cations in the condensate, and a degasifying treatment unit for removing carbon dioxide gas and hydrogen sulfide gas included in the condensate from which the cations have been removed.

6. The steam characteristics automatic measuring device according to claim 5, wherein the degasifying treatment comprises allowing nitrogen gas to bubble up in the condensate while the condensate is being heated.

7. A geothermal power-generating device comprising the steam characteristics automatic measuring device according to claim 1.

8. The steam characteristics automatic measuring device according to claim 1, further comprising a degasifying treatment unit for removing hydrogen sulfide gas from the condensate to be sent to the silica monitor.

9. The steam characteristics automatic measuring device according to claim 8, wherein the degasifying treatment comprises allowing nitrogen gas to bubble up in the condensate while the condensate is being heated.

10. The steam characteristics automatic measuring device according to claim 1, further comprising a pH meter for automatically measuring a pH value of the condensate, wherein the data processing transmitter automatically transmits data measured by the pH meter.

11. A steam characteristics automatic measuring device comprising:

an automatic non-condensable gas flowmeter for automatically and continuously measuring a total of a flow rate of non-condensable gas separated from steam taken out from under the ground by cooling the steam, wherein the steam is divided into the non-condensable gas and a condensate by the cooling, a thermometer for measuring a temperature of the condensate, a level detector for detecting a liquid level of the condensate and for outputting a lowest level-detecting signal when the liquid level falls to a lowest level and outputting a highest level-detecting signal when the liquid level rises to a highest level, and a processor for calculating a flow rate of saturated dissolved gas in the condensate based on the temperature, wherein the processor calculates a total flow rate of the non-condensable gas and the dissolved gas by adding the flow rate of non-condensable gas to the flow rate of saturated dissolved gas.

12. The steam characteristics automatic measuring device according to claim 11, wherein the processor calculates the amount of the dissolved gas from a flow rate of the condensate, the temperature, and a saturation concentration of the dissolved gas at the temperature.

13. The steam characteristics automatic measuring device according to claim 12, further comprising a data processing transmitter for automatically transmitting data corresponding to the total flow rate calculated by the processor.

14. The steam characteristics automatic measuring device according to claim 11, further comprising a data processing transmitter for automatically transmitting data corresponding to the total flow rate calculated by the processor.

15. A geothermal power-generating device comprising the steam characteristics automatic measuring device according to claim 11.

* * * * *